US012788500B2

(12) United States Patent
Fuentes-Ortega et al.

(10) Patent No.: US 12,788,500 B2
(45) Date of Patent: Nov. 10, 2026

(54) COCHLEAR IMPLANT WITH ONE OR MORE NAVIGATION SENSORS

(71) Applicant: Acclarent, Inc., Irvine, CA (US)

(72) Inventors: Cesar Fuentes-Ortega, Pasadena, CA (US); Henry F. Salazar, Pico Rivera, CA (US); Christopher A. Schutt, Bozeman, MT (US); George Gusein, Acre, IL (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 18/594,177

(22) Filed: Mar. 4, 2024

(65) Prior Publication Data

US 2024/0366312 A1 Nov. 7, 2024

Related U.S. Application Data

(60) Provisional application No. 63/464,260, filed on May 5, 2023.

(51) Int. Cl.

| | |
|---|---|
| ***A61N 1/05*** | (2006.01) |
| ***A61B 34/20*** | (2016.01) |
| ***A61B 90/00*** | (2016.01) |

(52) U.S. Cl.

CPC .............. *A61B 34/20* (2016.02); *A61B 90/37* (2016.02); *A61N 1/0541* (2013.01); *A61B 2034/2051* (2016.02)

(58) Field of Classification Search

CPC .............. A61N 1/36038–36039; A61N 1/0541
See application file for complete search history.

(56) References Cited

U.S. PATENT DOCUMENTS

| | | | | |
|---|---|---|---|---|
| 7,720,521 | B2 | 5/2010 | Chang et al. | |
| 7,751,865 | B2 | 7/2010 | Jascob et al. | |
| 8,886,330 | B2 * | 11/2014 | Taylor | A61N 1/0541 607/57 |
| 9,345,397 | B2 * | 5/2016 | Taylor | A61B 1/227 |
| 9,775,539 | B2 | 10/2017 | Carter | |
| 9,999,770 | B2 | 6/2018 | Walraevens et al. | |
| 10,463,242 | B2 | 11/2019 | Kesten et al. | |
| 10,561,370 | B2 | 2/2020 | Salazar et al. | |
| 10,751,132 | B2 * | 8/2020 | Tsay | A61N 1/36038 |
| 10,773,082 | B2 | 9/2020 | Tsay et al. | |
| 10,987,513 | B2 | 4/2021 | Kaufmann et al. | |
| 11,185,693 | B2 * | 11/2021 | Tsay | A61B 90/37 |
| 11,406,456 | B2 * | 8/2022 | Tsay | A61B 34/20 |
| 11,484,714 | B2 * | 11/2022 | Tsay | A61N 1/36039 |
| 2004/0024309 | A1 * | 2/2004 | Ferre | A61B 5/062 600/424 |
| 2012/0071890 | A1 * | 3/2012 | Taylor | A61B 5/6844 606/129 |

(Continued)

*Primary Examiner* — Angela M Hoffa
(74) *Attorney, Agent, or Firm* — Morgan, Lewis & Bockius LLP

(57) ABSTRACT

An apparatus includes an elongate body. A distal portion of the elongate body is configured to fit in a cochlea of a patient. A plurality of stimulation elements are positioned along the distal portion of the elongate body. The stimulation elements are operable to stimulate auditory nerves in the cochlea of the patient. One or more position sensors are positioned along the elongate body. Each position sensor of the one or more position sensors is configured to generate a signal indicating a position of the position sensor in three-dimensional space.

13 Claims, 4 Drawing Sheets

(56) References Cited

U.S. PATENT DOCUMENTS

| | | | | |
|---|---|---|---|---|
| 2014/0228669 | A1* | 8/2014 | Carter | A61N 1/0541 600/409 |
| 2014/0350640 | A1* | 11/2014 | Patrick | A61N 1/0541 607/57 |
| 2015/0025546 | A1* | 1/2015 | Taylor | A61N 1/0541 606/129 |
| 2015/0049888 | A1* | 2/2015 | Johnston | A61N 1/36038 381/312 |
| 2015/0320550 | A1* | 11/2015 | Downing | A61N 1/0541 607/137 |
| 2017/0151022 | A1 | 6/2017 | Jascob et al. | |
| 2017/0180882 | A1 | 6/2017 | Lunner et al. | |
| 2019/0239959 | A1* | 8/2019 | Tsay | A61N 1/37229 |
| 2019/0240488 | A1* | 8/2019 | Tsay | A61B 34/20 |
| 2019/0240489 | A1* | 8/2019 | Tsay | A61N 1/36039 |
| 2020/0323595 | A1* | 10/2020 | Tsay | A61N 1/36038 |
| 2020/0406038 | A1* | 12/2020 | Tsay | A61B 90/37 |
| 2023/0028220 | A1* | 1/2023 | Chen | A61N 5/0622 |
| 2024/0099606 | A1* | 3/2024 | Bar-Tal | A61B 34/20 |

* cited by examiner

COCHLEAR IMPLANT WITH ONE OR MORE NAVIGATION SENSORS

PRIORITY

This application claims priority to U.S. Provisional Pat. App. No. 63/464,260, entitled "Cochlear Implant with One or More Navigation Sensors," filed May 5, 2023, the disclosure of which is incorporated by reference herein, in its entirety.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation system that may be used in IGS procedures is the CARTO® 3 System by Biosense-Webster, Inc., of Irvine, California. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, some instruments can include sensors (e.g., electromagnetic coils that emit electromagnetic fields and/or are responsive to externally generated electromagnetic fields), which can be used to perform the procedure while the sensors send data to the computer indicating the current position of each sensor-equipped instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

In some scenarios where a medical procedure is to be performed at a lateral side of a head of a patient (e.g., otology procedures, neurotology procedures, lateral skull base procedures, etc.), it may be desirable to perform the IGS system registration process at the lateral side of the head of the patient. Such registration may provide enhanced accuracy during subsequent IGS system navigation with sensor-equipped instruments that are inserted into the patient's head via the lateral side of the head of the patient. While several systems and methods have been made and used in connection with IGS navigation systems, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Example of an Image Guided Surgery Navigation System

Figure 1:
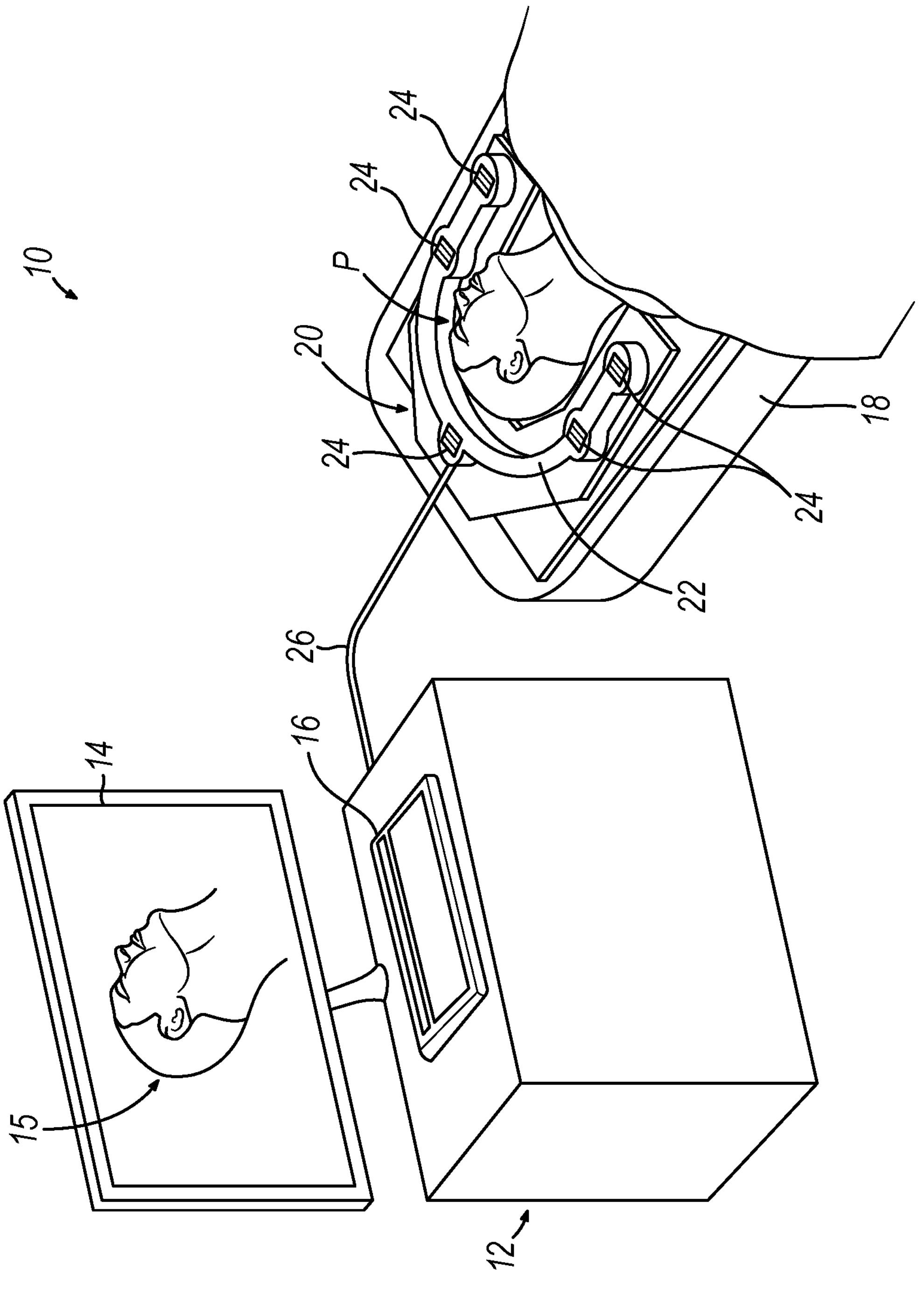
FIG. 1 depicts a schematic view of an example of a surgery navigation system with a patient lying on their side.

When performing a medical procedure within a head of a patient (P), it may be desirable to have information regarding the position of an instrument within the head of the patient (P), particularly when the instrument is in a location where it is difficult or impossible to obtain an endoscopic view of a working element of the instrument within the head of the patient (P). FIG. 1 shows an example of an IGS navigation system (10) enabling a medical procedure to be performed within a head of a patient (P) using image guidance. In addition to or in lieu of having the components and operability described herein IGS navigation system (50) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein, in its entirety; and/or U.S. Pat. No. 10,561,370, entitled "Apparatus to Secure Field Generating Device to Chair," issued Feb. 18, 2020, the disclosure of which is incorporated by reference herein, in its entirety.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head of the patient (P). An instrument, such as any of the instruments described below, may be inserted into the head of the patient (P). Such an instrument may be a standalone device or may be positioned on an end effector. In the present example, frame (22) is positioned on a table (18), with the patient (P) lying on their side on table (18) such that frame (42) is located adjacent to the head of the patient.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from the instrument to determine the location of a navigation sensor or position sensor in the instrument within the head of the patient (P). Processor (12) comprises a processing unit (e.g., a set of electronic circuits arranged to evaluate and execute software instructions using combinational logic circuitry or other similar circuitry) communicating with one or more memories. Processor (12) is coupled with field generator assembly (20) via a cable (26) in this example, though processor (12) may alternatively be coupled with field generator assembly (20) wirelessly or in any other suitable fashion.

A display screen (14) and user input feature (16) are also coupled with processor (12) in this example. User input feature (16) may comprise a keyboard, a mouse, a trackball, and/or any other suitable components, including combinations thereof. In some versions, display screen (14) is in the form of a touchscreen that is operable to receive user inputs, such that display screen (14) may effectively form at least part of user input feature (160). A physician may use input feature (16) to interact with processor (12) while performing a registration process, while performing a medical procedure, and/or at other suitable times.

As described in greater detail below, a medical instrument may include a navigation sensor or position sensor that is responsive to positioning within the alternating magnetic fields generated by field generators (24). In some versions, the navigation sensor or position sensor of the instrument may comprise at least one coil at or near the distal end of the instrument. When such a coil is positioned within an alternating electromagnetic field generated by field generators (24), the alternating magnetic field may generate electrical current in the coil, and this electrical current may be communicated as position-indicative signals via wire or wirelessly to processor (12). This phenomenon may enable IGS navigation system (10) to determine the location of the distal end of the instrument within a three-dimensional space (i.e., within the head of the patient (P), etc.). To accomplish this, processor (12) executes an algorithm to calculate location coordinates of the distal end of the instrument from the position related signals of the coil(s) in the instrument. Thus, a navigation sensor may serve as a position sensor by generating signals indicating the real-time position of the sensor within three-dimensional space.

Processor (12) uses software stored in a memory of processor (12) to calibrate and operate IGS navigation system (10). Such operation includes driving field generators (24), processing data from the instrument, processing data from user input feature (16), and driving display screen (14). In some implementations, operation may also include monitoring and enforcement of one or more safety features or functions of IGS navigation system (10). Processor (12) is further operable to provide video and/or other images in real time via display screen (14), showing the position of the distal end of the instrument in relation to a video camera image of the head of the patient (P), in relation to preoperative image (e.g., a CT scan image) of the head of the patient (P), and/or in relation to a computer-generated three-dimensional model of anatomical structures of the head of the patient (P). Display screen (14) may display such images simultaneously and/or superimposed on each other during the medical procedure. Such displayed images may also include graphical representations of instruments that are inserted in the head of the patient (P), or at least a position indicator (e.g., crosshairs, etc.), such that the operator may observe a visual indication of the instrument at its actual location in real time via display screen (14).

In the example shown in FIG. 1, display screen (14) is displaying a three-dimensional rendering (15) of the head of the patient (P). By way of further example only, display screen (14) may provide images in accordance with at least some of the teachings of U.S. Pat. No. 10,463,242, entitled "Guidewire Navigation for Sinuplasty," issued Nov. 5, 2019, the disclosure of which is incorporated by reference herein, in its entirety. In the event that the operator is also using an endoscope, the endoscopic image may also be provided on display screen (14). The images provided through display screen (14) may thus help guide the operator in maneuvering and otherwise manipulating instruments within the head of the patient (P).

In the present example, field generators (24) are in fixed positions relative to the head of the patient (P), such that the frame of reference for IGS navigation system (10) (i.e., the electromagnetic field generated by field generators (24)) does not move with the head of the patient (P). In some instances, the head of the patient (P) may not remain completely stationary relative to field generators (24) throughout the duration of a medical procedure, such that it may be desirable to track movement of the head of the patient (P) during a medical procedure. To that end, IGS navigation system (10) of the present example includes a tracking sensor (28) that is fixedly secured to the head of the patient (P). Tracking sensor (28) includes one or more coils and/or other position sensors that are operable to generate signals in response to the alternating magnetic fields generated by field generators (24), with such signals indicating the position of tracking sensor (28) in three-dimensional space. In the present example, these signals are communicated to processor (12) via a cable (29). In some other versions, these signals are communicated to processor (12) wirelessly.

Regardless of how processor (12) receives signals from tracking sensor (28), processor (12) may utilize such signals to effectively track the real-time position of the head of the patient (P) and thereby account for any movement of the head of the patient (P) during a medical procedure. In other words, processor (12) may process position-indicative signals from tracking sensor (28) in combination with position-indicative signals from a position sensor-equipped medical instrument that is disposed in the head of a patient (P) to accurately determine the real-time position of the distal end (or other working feature) of the medical instrument in the head of the patient (P) despite any movement of the head of the patient (P) during the medical procedure.

In the example shown in FIG. 1, tracking sensor (28) is positioned posterior to the ear (E) of the patient (P), though it should be understood that tracking sensor (28) may be positioned at any other suitable location on the head of the patient (P). By way of example only, tracking sensor (28) may alternatively be positioned at the lateral forehead, at the upper orbital rim, or at some other location near the site at which the medical procedure will be performed in the head of the patient (P). In some variations, a tracking sensor (28) is positioned in the mouth of the patient (P). It should also be understood that tracking sensor (28) may be fixedly secured to the head of the patient in numerous ways, including but not limited to adhesives, screws, tacks, sutures, etc.

II. Overview of Cochlear Implant

Figure 2:
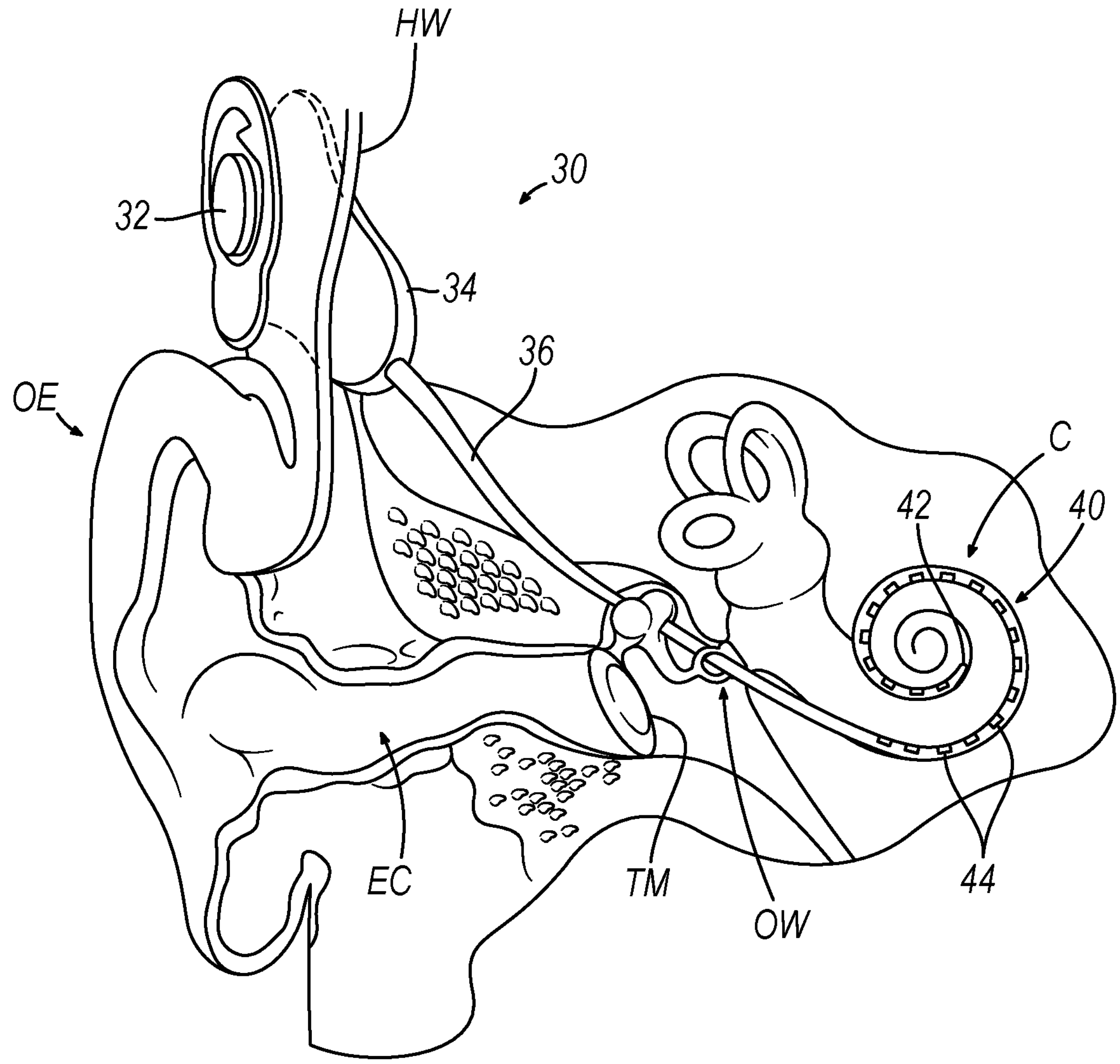
FIG. 2 depicts a schematic view of an example of a cochlear implant assembly installed in the head of a patient.

In some patients with hearing loss, a cochlear implant device may be installed to stimulate nerve cells in the cochlea of the patient to thereby provide at least some enhanced ability for the patient to hear. FIG. 2 shows an example of such a cochlear implant device (30). Cochlear implant device (30) of this example in includes an external transmitter (32) and an internal transceiver (34). External transmitter (32) is positioned external to the head wall (HW) (i.e., skin and skull, etc.) of the patient (P), near the outer ear (OE). External transmitter (32) may be coupled with one or more sound input features (e.g., one or more microphones, telecoils, etc.), which may also be positioned external to the head wall (HW) of the patient (P). Internal transceiver (34) is fixedly position internally to at least a portion of the head wall (HW) of the patient (P). In some cases, internal transceiver (34) is under the skin of the patient yet external to the skull of the patient. By way of further example only, internal transceiver (34) may be positioned in a recess of a temporal bone of the patient.

External transmitter (32) and internal transceiver (34) are operable to communicate wirelessly (e.g., via transmitting/receiving coils). Such wireless communication may include audio signals and/or electrical power from external transmitter (32) to internal transceiver (34). External transmitter (32) and internal transceiver (34) may also include complementary magnets to promote positional alignment of external transmitter (32) with internal transceiver (34).

An elongate body (36) extends from internal transceiver (34) and passes through the oval window (OW), such that elongate body (36) reaches the inner ear of the patient without traversing the ear canal (EC) or the tympanic membrane (TM). By way of example only, elongate body (36) may be inserted through an opening that is created through the patient's mastoid bone to access the middle ear cavity of the patient. An electrode assembly (40) positioned at a distal portion of elongate body (36) is disposed in the cochlea (C). While elongate body (36) reaches the cochlea (C) via the oval window (OW) in this example, elongate body (36) may alternatively reach the cochlea (C) via any other suitable path (e.g., the round window, the promontory, etc.). Electrode assembly (40) is substantially flexible to conform to the spiral curve of the interior of the cochlea (C), without imparting trauma to the wall of the cochlea (C). Electrode assembly (40) includes a plurality of electrical contacts (44) that are proximal to distal tip (42). These electrical contacts (44) are operable to stimulate auditory nerve cells in the cochlea (C), bypassing absent or defective hair cells that normally transduce acoustic vibrations into neural activity. In particular, cochlear implant device (30) may be operable to convert sound detected via one or more sound input features (e.g., one or more microphones, telecoils, etc.) into electrical signals, transmit the electrical signals wirelessly from external transmitter (32) to internal transceiver (34), and apply corresponding electrical signals to auditory nerve cells in the cochlea (C) via electrical contacts (44). Such auditory nerve cell stimulation may effectively provide the patient with some level of hearing that they would not otherwise have vin the absence of cochlear implant device (30).

By way of further example only, cochlear implant device (30) may be constructed and operable in accordance with at least some of the teachings of U.S. Pat. No. 9,999,770, entitled "Cochlear Implant Electrode Array Including Receptor and Sensor," issued Jun. 19, 2018, the disclosure of which is incorporated by reference herein, in its entirety.

III. Examples of Cochlear Implant with Position Sensors

As noted above, elongate body (36) may be inserted through an opening that is created through the patient's mastoid bone to access the middle ear cavity of the patient, and passed through the oval window (OW) (or other pathway) to insert electrode assembly (40) in the cochlea (C). Even with elongate body (36) being flexible and with distal tip (42) being atraumatic, it may be difficult to successfully navigate electrode assembly (40) into the cochlea (C), particularly since direct visualization might not be possible. In other words, it may be beneficial to provide a version of cochlear implant device (30) that is compatible with IGS system (10), such that the operator may monitor the real-time position of elongate body (36) in relation to one or more preoperative images as the operator advances electrode assembly (40) toward and into the cochlea (C). It may also be beneficial to enable the operator to utilize IGS system (10) to re-assess the real-time position of cochlear implant device (30) after cochlear implant device (30) has been installed in the patient (P). In addition, it may be beneficial to enable the operator to utilize IGS system (10) to track the real-time position of cochlear implant device (30) during repositioning of cochlear implant device (30) within the patient (P); or during removal of cochlear implant device (30) from the patient (P). The following provides examples of how cochlear implant device (30) may be modified to provide such compatibility with IGS system (10).

Figure 3:
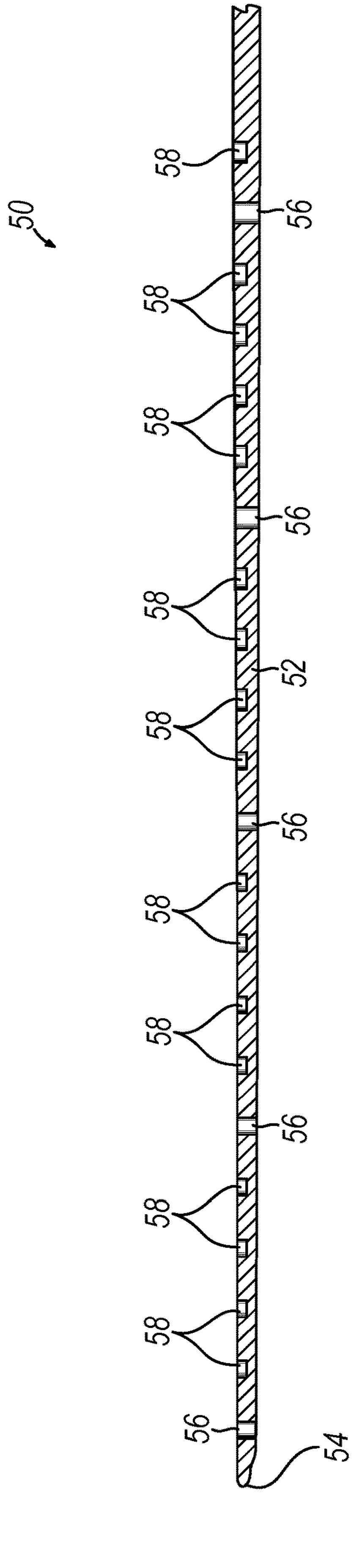
FIG. 3 depicts a side elevation view of an example of a distal portion of an electrode assembly that may be incorporated into the cochlear implant assembly of FIG. 2, with the distal portion in a straight configuration.

FIG. 3 depicts an example of an electrode assembly (50) that may be incorporated into electrode assembly (40) of elongate body (36). Electrode assembly (50) of this example includes a flexible elongate body (52), which may be similar to elongate body (36). Electrode assembly (50) of this example terminates in a distal tip (54), which may be similar to distal tip (42). Electrode assembly (50) of this example further includes a plurality of electrode contacts (58), which may be similar to electrical contacts (44). Unlike electrode assembly (40) of elongate body (36), electrode assembly (50) of this example further includes a plurality of position sensors (56). In some versions, each position sensor (56) includes one or more coils that are operable to generate signals in response to the alternating magnetic fields generated by field generators (24), with such signals indicating the position of position sensor (56) in three-dimensional space. In other words, processor (12) is operable to determine the real-time position of each position sensor (56) in three-dimensional space; and may thereby render indications of such positions on display screen (14). By way of further example only, processor (12) may provide such indications on a three-dimensional rendering (15) of the head of the patient (P) and/or in one or more pre-operative images of the associated anatomy of the patient (P).

In the example shown in FIG. 3, one position sensor (56) is positioned near distal tip (54), while several other position sensors (56) are positioned along the length elongate body (52) between groups of electrode contacts (58). In some other versions, only the distal-most position sensor (56) is included, such that the other position sensors (56) depicted in FIG. 3 are omitted. It should be understood that any suitable number of position sensors may be positioned at any suitable locations along elongate body (52). It should also be understood that, with a plurality of position sensors (56) being incorporated into elongate body (52), it may be possible to determine the real-time shape or pose of elongate body (52), which may further assist in determining the depth of insertion of elongate body (52) in the cochlea (C).

Figure 4:
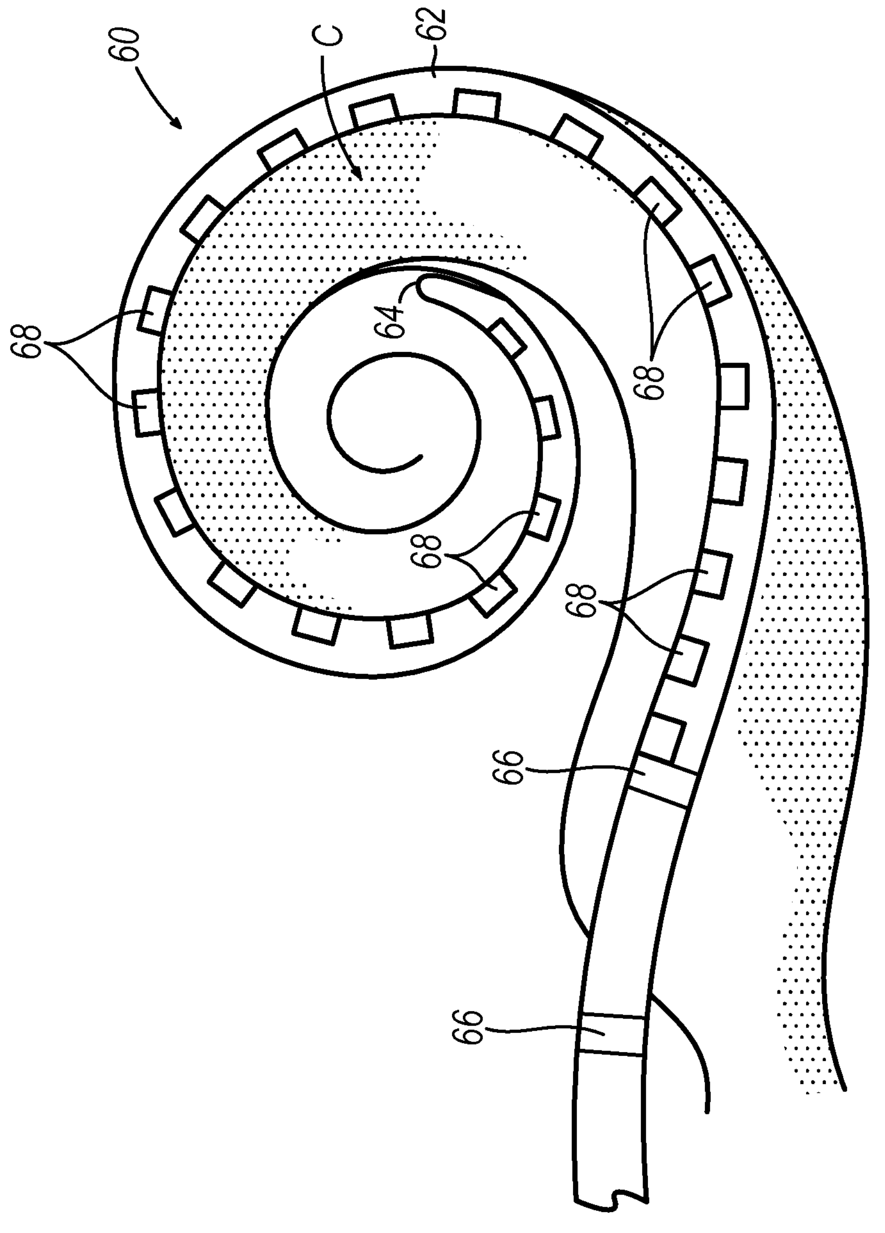
FIG. 4 depicts a schematic view of another example of a distal portion of an electrode assembly that may be incorporated into the cochlear implant assembly of FIG. 2, with the distal portion installed in a cochlea of a patient.

FIG. 4 shows another example of an electrode assembly (60) that may be incorporated into electrode assembly (40) of elongate body (36). Electrode assembly (60) of this example includes a flexible elongate body (62), which may be similar to elongate body (36). Electrode assembly (60) of this example terminates in a distal tip (64), which may be similar to distal tip (42). Electrode assembly (60) of this example further includes a plurality of electrode contacts (68), which may be similar to electrical contacts (44). Unlike electrode assembly (40) of elongate body (36), electrode assembly (60) of this example further includes a plurality of position sensors (66). In some versions, each position sensor (66) includes one or more coils that are operable to generate signals in response to the alternating magnetic fields generated by field generators (24), with such signals indicating the position of position sensor (66) in three-dimensional space. In other words, processor (12) is operable to determine the real-time position of each position sensor (56) in three-dimensional space; and may thereby render indications of such positions on display screen (14). By way of further example only, processor (12) may provide such indications on a three-dimensional rendering (15) of the head of the patient (P) and/or in one or more pre-operative images of the associated anatomy of the patient (P).

Unlike position sensors (56) of electrode assembly (50), position sensors (66) of electrode assembly (60) are positioned proximal to all electrode contacts (68) of electrode assembly (60). This positioning of position sensors (66) on elongate body (62) may nevertheless provide sufficient data on the real-time position of electrode assembly (60) during installation of electrode assembly (60) in the head of the patient (P).

Regardless of which form of electrode assembly (50, 60) is being used, the operator may track the real-time position of electrode assembly (50, 60) via IGS system (10) as electrode assembly (50, 60) is inserted through the opening that is created through the patient's mastoid bone, then further through the oval window (OW) (or other pathway), until electrode assembly (50, 60) is sufficiently disposed in the cochlea (C). Such use of IGS system (10) may include visual observation of display screen (14), which may render indicators showing the real-time position of one or more portions of electrode assembly (50, 60) overlaid on three-dimensional rendering (15) of the head of the patient (P) and/or on one or more pre-operative images of the associated anatomy of the patient (P), based on signals from position sensors (56, 66).

In some cases, signals from position sensors (56, 66) are only utilized during the process of installing cochlear implant (30) in the head of the patient (P). Thus, after cochlear implant (30) is installed in the head of the patient (P), position sensors (56, 66) are no longer utilized. Also in some cases, position sensors (56, 66) are coupled with processor (12) via internal transceiver (34) during the process of installing cochlear implant (30) in the head of the patient (P). In some such cases, a wireless coupling is achieved between internal transceiver (34) and processor (12). In some other cases, a wire is temporarily coupled with internal transceiver (34) to thereby couple internal transceiver (34) with processor (12); and this wire is removed after cochlear implant (30) is installed in the head of the patient (P). Alternatively, position sensors (56, 66) of electrode assembly (50, 60) may achieve communication with processor (12) in any other suitable fashion.

While some scenarios may only warrant processing of signals from position sensors (56, 66) during the process of installing cochlear implant (30) in the head of the patient (P), some other scenarios may warrant processing of signals from position sensors (56, 66) after the process of installing cochlear implant (30) in the head of the patient (P). For instance, an operator may wish to confirm whether electrode assembly (50, 60) remains in a desired position within the cochlea (C) at some point after cochlear implant (30) has been installed in the head of the patient (P). The operator may thus check the position of electrode assembly (50, 60) within the cochlea (C) based on signals from position sensors (56, 66). In cases where it is necessary to adjust the position of an already-installed cochlear implant (30), signals from position sensors (56, 66) may be monitored to facilitate such adjustment to ensure that electrode assembly (50, 60) eventually reaches the desired position within the cochlea (C) through the adjustment process. In the event that removal of cochlear implant (30) from the head of the patient (P) is warranted, signals from position sensors (56, 66) may be monitored to facilitate such removal. Alternatively, signals from position sensors (56, 66) may be utilized in other scenarios in any other suitable fashion.

As another example of a variation, electrode assembly (40) may be configured such that electrical contacts (44) may serve as position sensors during installation of cochlear implant (30) in the head of the patient (P); then transition to a role of stimulating auditory nerve cells in the cochlea (C) after installation is complete. By way of example only, electrical contacts (44) may be provided in the form of exposed coil-shaped traces on a flex circuit substrate about elongate body (36). Such coil-shaped traces may be configured to generate position-indicative signals in response to alternating magnetic fields from field generators (24) while in a position sensing mode. Such coil-shaped traces may be further configured to sufficiently contact and stimulate the auditory nerve cells in the cochlea (C) while in a stimulating mode. The coil-shaped traces may be operatively toggled from the position sensing mode to the stimulating mode manually by the operator after installation is complete. Alternatively, the coil-shaped traces may be operatively toggled from the position sensing mode to the stimulating mode automatically (e.g., by processor (12) or by some other component) after the position signals from the coil-shaped traces indicate that the installation is complete. The foregoing examples are merely illustrative, such that an electrical contact or other stimulation feature may serve an additional role as a position sensor in any other suitable fashion.

While electrical contacts (44, 58, 68) provide auditory nerve stimulation in the cochlea (C) in this example, any other suitable form of stimulation element may be used, including but not limited to optical stimulation elements or vibratory stimulation elements. Moreover, more than one type of stimulation element may be incorporated into a cochlear implant device (30). The inclusion of position sensors (56, 66) is not dependent on the type of stimulation element incorporated into cochlear implant device (30).

IV. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) an elongate body, a distal portion of the elongate body being configured to fit in a cochlea of a patient; (b) a plurality of stimulation elements along the distal portion of the elongate body, the stimulation elements being operable to stimulate auditory nerves in the cochlea of the patient; and (c) one or more position sensors along the elongate body, each position sensor of the one or more position sensors being configured to generate a signal indicating a position of the position sensor in three-dimensional space.

Example 2

The apparatus of Example 1, the elongate body being flexible.

Example 3

The apparatus of any of Examples 1 through 2, the elongate body having an atraumatic distal tip.

Example 4

The apparatus of any of Examples 1 through 3, the stimulation elements comprising electrode contacts.

Example 5

The apparatus of any of Examples 1 through 4, the one or more position sensors being longitudinally interposed between the stimulation elements.

Example 6

The apparatus of any of Examples 1 through 5, the one or more position sensors including a distal position sensor positioned distal to the plurality of stimulation elements.

Example 7

The apparatus of any of Examples 1 through 6, the one or more position sensors including a proximal position sensor positioned proximal to the plurality of stimulation elements.

Example 8

The apparatus of any of Examples 1 through 7 the one or more position sensors comprising a coil.

Example 9

The apparatus of Example 8, the coil being configured to generate a signal indicating a position of the position sensor in three-dimensional space in response to an electromagnetic field.

Example 10

A method, comprising: (a) inserting an elongate member into a head of a patient along an insertion path; (b) tracking a position of the elongate member along the insertion path based on signals from one or more position sensors integrated into the elongate member; and (c) while tracking the position of the elongate member along the insertion path based on signals from the one or more position sensors integrated into the elongate member, positioning a distal portion of the elongate member in a cochlea of the patient.

Example 11

The method of Example 10, the insertion path including an opening in a mastoid bone of the patient.

Example 12

The method of any of Examples 10 through 11, the insertion path including an oval window of a middle ear of the patient.

Example 13

The method of any of Examples 10 through 11, the insertion path including a round window of a middle ear of the patient.

Example 14

The method of any of Examples 10 through 13, the insertion path including a promontory of a tympanic cavity of the patient.

Example 15

The method of any of Examples 10 through 14, the act of tracking a position of the elongate member along the insertion path based on signals from one or more position sensors integrated into the elongate member comprising generating an electromagnetic field around the head of the patient, the signals from the position sensors being generated in response to the electromagnetic field.

Example 16

The method of any of Examples 10 through 15, the act of tracking a position of the elongate member along the insertion path based on signals from one or more position sensors integrated into the elongate member comprising observing a display screen, the display screen showing at least one indicator representing a position of a corresponding portion of the elongate member in the patient.

Example 17

The method of Example 16, the display screen further including at least one image of at least a portion of the head of the patient, the at least one image being overlaid on the at least one image of at least a portion of the head of the patient.

Example 18

The method of Example 17, the at least one image of at least a portion of the head of the patient including a preoperative image.

Example 19

The method of any of Examples 17 through 18, the at least one image of at least a portion of the head of the patient including a three-dimensional model of at least a portion of the head of the patient.

Example 20

The method of any of Examples 10 through 19, the distal portion of the elongate member further comprising a plurality of electrode contacts, the act of positioning the distal portion of the elongate member in the cochlea of the patient comprising positioning the electrode contacts to enable the electrode contacts to stimulate nerve cells in the cochlea of the patient.

Example 21

The method of Example 20, further comprising implanting a receiver in the head of the patient, the receiver being configured to generate electrical signals and transmit the generated electrical signals to the electrode contacts.

Example 22

The method of Example 21, the implanted receiver being positioned in a recess of a temporal bone in the head of the patient.

Example 23

The method of any of Examples 10 through 22, further comprising checking a position of the elongate member, based on signals from the one or more position sensors integrated into the elongate member, after the distal portion of the elongate member has been positioned in the cochlea of the patient.

Example 24

The method of any of Examples 10 through 23, further comprising readjusting the position of the distal portion of the elongate member in the cochlea of the patient after the distal portion of the elongate member has been positioned in the cochlea of the patient.

Example 25

The method of Example 24, further comprising tracking the position of the elongate member, based on signals from the one or more position sensors integrated into the elongate member, during the act of readjusting.

Example 26

The method of any of Examples 10 through 25, further comprising removing the distal portion of the elongate member from the cochlea of the patient after the distal portion of the elongate member has been positioned in the cochlea of the patient.

Example 27

The method of Example 26, further comprising tracking the position of the elongate member, based on signals from the one or more position sensors integrated into the elongate member, during the act of removing.

Example 28

A system comprising: (a) a cochlear implant device, the cochlear implant device comprising: (i) an elongate body, a distal portion of the elongate body being configured to fit in a cochlea of a patient, (ii) a plurality of stimulation elements along the distal portion of the elongate body, the stimulation elements being operable to stimulate auditory nerves in the cochlea of the patient, and (iii) one or more position sensors along the elongate body, each position sensor of the one or more position sensors being configured to generate a signal indicating a position of the position sensor in three-dimensional space; (b) a processor, the processor being configured to receive signals generated by the one or more position sensors; and (c) a display screen, the processor being further configured to drive the display screen to display one or more indicators representing a real-time position of at least a portion of the elongate body in three-dimensional space, based at least in part on the received signals generated by the one or more position sensors.

Example 29

The system of Example 28, further comprising a field generating assembly, the field generating assembly being operable to generate an electromagnetic field around a head of the patient, the one or more position sensors being configured to generate the signals in response to the electromagnetic field.

Example 30

The system of any of Examples 28 through 29, the stimulation elements comprising electrode contacts, the electrode contacts being configured to stimulate nerves in the cochlea of the patient.

V. Miscellaneous

It should be understood that any of the teachings, expressions, embodiments, examples, etc. described herein may be combined with any of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and scaled container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

an elongate body, a distal portion of the elongate body being configured to fit in a cochlea of a patient;

a plurality of stimulation elements along the distal portion of the elongate body, the stimulation elements being operable to stimulate auditory nerves in the cochlea of the patient;

two or more position sensors along the elongate body, each position sensor of the two or more position sensors being configured to generate a signal indicating a position of the position sensor in three-dimensional space relative to the head of the patient, the two or more position sensors including a first position sensor and a second position sensor that are both (i) positioned proximal to all of the plurality of stimulation elements and (ii) longitudinally spaced apart from each other.

2. The apparatus of claim 1, the elongate body being flexible.

3. The apparatus of claim 1, the elongate body having an atraumatic distal tip.

4. The apparatus of claim 1, the stimulation elements comprising electrode contacts.

5. The apparatus of claim 1, each of the two or more position sensors comprising a coil.

6. The apparatus of claim 5, the coil being configured to generate a signal indicating a position of the position sensor in three-dimensional space relative to the head of the patient in response to an electromagnetic field.

7. The apparatus of claim 1, further comprising one or more magnetic field generators configured to generate alternating magnetic fields around the head of the patient.

8. The apparatus of claim 1, wherein the first position sensor and the second position sensor are longitudinally spaced apart from each other without any of the plurality of stimulation elements positioned therebetween.

9. The apparatus of claim 1, further comprising a tracking sensor configured to be fixedly secured to a head of the patient, the tracking sensor including a coil configured to generate a tracking signal indicating a position of the tracking sensor in three- dimensional space relative to the head of the patient.

10. The apparatus of claim 1, further comprising a tracking sensor configured to be fixedly secured to a head of the patient, the tracking sensor being configured to track a position of the head relative to the two or more position sensors.

11. The apparatus of claim 1, further comprising a tracking sensor configured to be fixedly secured to a head of the patient and positioned posterior to an ear of the head of the patient.

12. The apparatus of claim 1, further comprising a tracking sensor configured to be fixedly secured to a head of the patient, the tracking sensor being positioned at a lateral forehead of the head of the patient or at an upper orbital rim of the head of the patient.

13. The apparatus of claim 9, further comprising a processor configured to receive the signal from the two or more position sensors and the tracking signal from the tracking sensor, and to track the position of the two or more position sensors in real-time despite any movement of the head of the patient.

* * * * *